United States Patent
Kato et al.

(10) Patent No.: US 8,906,519 B2
(45) Date of Patent: Dec. 9, 2014

(54) OLIGOANILINE COMPOUNDS

(75) Inventors: Taku Kato, Funabashi (JP); Takuji Yoshimoto, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 806 days.

(21) Appl. No.: 12/441,037

(22) PCT Filed: Sep. 5, 2007

(86) PCT No.: PCT/JP2007/067276
§ 371 (c)(1),
(2), (4) Date: Mar. 12, 2009

(87) PCT Pub. No.: WO2008/032616
PCT Pub. Date: Mar. 20, 2008

(65) Prior Publication Data
US 2010/0159279 A1    Jun. 24, 2010

(30) Foreign Application Priority Data

Sep. 13, 2006   (JP) ................................ 2006-247679

(51) Int. Cl.
| | |
|---|---|
| *B32B 9/04* | (2006.01) |
| *C07C 211/54* | (2006.01) |
| *C07C 213/00* | (2006.01) |
| *C07C 217/92* | (2006.01) |
| *H05B 33/22* | (2006.01) |
| *C07D 493/18* | (2006.01) |
| *C07C 211/55* | (2006.01) |
| *H01L 51/00* | (2006.01) |
| *C07C 323/37* | (2006.01) |
| *H01L 51/50* | (2006.01) |

(52) U.S. Cl.
CPC ........... *C07C 323/37* (2013.01); *H01L 51/5048* (2013.01); *C07C 217/92* (2013.01); *H05B 33/22* (2013.01); *C07D 493/18* (2013.01); *C07C 211/55* (2013.01); *H01L 51/0059* (2013.01); *H01L 51/0035* (2013.01)
USPC ............ 428/690; 428/704; 564/434; 564/430

(58) Field of Classification Search
USPC ................................... 428/704; 564/434, 430
See application file for complete search history.

(56) References Cited

U.S. PATENT DOCUMENTS

| | | | |
|---|---|---|---|
| 2,103,188 | A | 12/1937 | Semon |
| 2,394,257 | A | 2/1946 | Parker |
| 5,605,992 | A | 2/1997 | Urashima et al. |
| 2005/0082514 | A1* | 4/2005 | Yoshimoto et al. ........... 252/500 |

FOREIGN PATENT DOCUMENTS

| | | | | |
|---|---|---|---|---|
| EP | 1 640 372 A1 | 3/2006 | | |
| JP | 7-316209 A | 12/1995 | | |
| JP | 10-88123 A | 4/1998 | | |
| JP | 2002-151256 A | 5/2002 | | |
| JP | 2002-151272 | * | 5/2002 | ............. H05B 33/22 |
| JP | 2002-151272 A | 5/2002 | | |
| JP | 2005-108828 A | 4/2005 | | |
| WO | WO-2005/000832 A1 | 1/2005 | | |
| WO | WO-2006/025342 A1 | 3/2006 | | |

OTHER PUBLICATIONS

Machine English translation of JP 2002-151272. Apr. 18, 2011.*
European Search Report dated Sep. 6, 2010, in connection with PCT International Application No. PCT/JP2007/067276.
Fenxi Huaxue, Chinese Journal of Analytical Chemistry, 2000, vol. 28, No. 8, pp. 956-959.
Ochi et al., "Preparation of Linear Oligoaniline Derivatives Using Titanium Alkoxide as a Condensing Agent", Bulletin of Chemical Society of Japan, 1994, vol. 67, pp. 1749-1752.
Japanese Office Action for Japanese Application No. 2008-534299 dated Oct. 24, 2012.

* cited by examiner

*Primary Examiner* — J. L. Yang
(74) *Attorney, Agent, or Firm* — Birch, Stewart, Kolasch & Birch, LLP

(57) ABSTRACT

An oligoaniline compound represented by the formula (1) can provide a charge transporting thin film which shows a suppressed coloration in the visible range. Use of this thin film makes it possible to ensure a color reproducibility of a device without lowering the color purity of an electroluminescent light or a light having passed through a color filter.

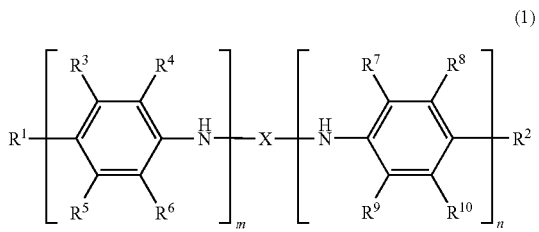
(1)

wherein $R^1$ to $R^{10}$ independently represent each a hydrogen atom, a halogen, etc.; m and n independently represent each an integer of 1 or more while satisfying the condition $m+n \leq 20$; and X is a structure represented by any of the following formulae (4) to (10), etc.;

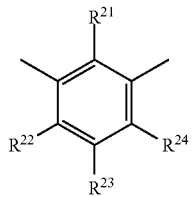
(4)

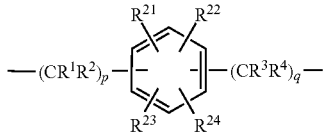
(5)

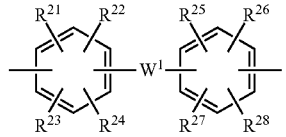
(6)

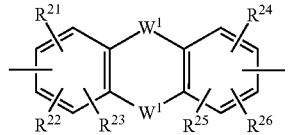
(7)

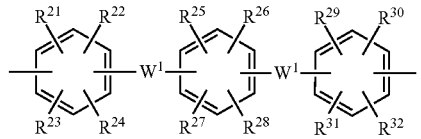
(8)

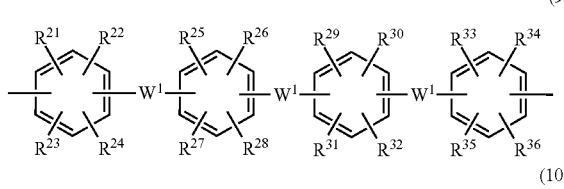
(9)

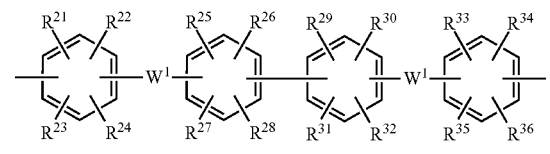
(10)

wherein $R^{21}$ to $R^{36}$ independently represent each a hydrogen atom, a hydroxyl group, etc.; p and q represent each an integer of 1 or more while satisfying the conditions $p \leq 20$ and $q \leq 20$; and $W^1$s independently represent each —$(CR^1R^2)p$-, —O—, —S—, etc.

10 Claims, 1 Drawing Sheet

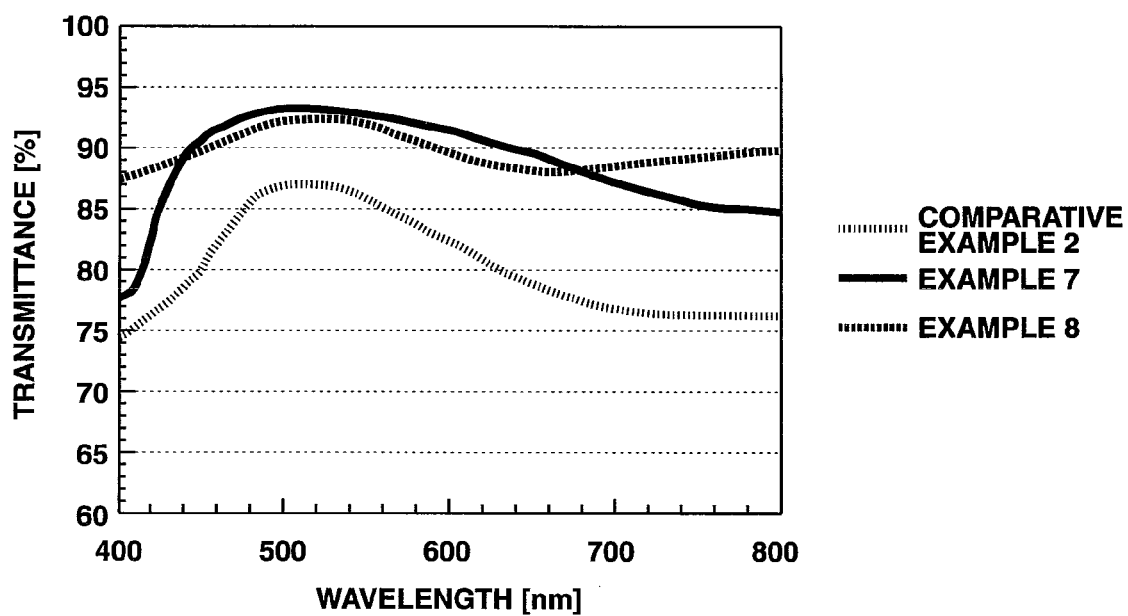

OLIGOANILINE COMPOUNDS

TECHNICAL FIELD

This invention relates to an oligoaniline compound and more particularly, to an oligoaniline compound having a structural unit different from an aniline skeleton in the repeating units of aniline.

BACKGROUND ART

We have already reported that a charge-transporting thin film obtained from an organic solvent-based charge-transporting varnish making use of a charge transport material made of a low molecular weight oligoaniline compound exhibits excellent electroluminescent device characteristics (see Patent Document 1: JP-A 2002-151272).

In the charge-transporting varnish of Patent Document 1, the low molecular weight oligoaniline compound serving as a charge transport material has a structure of the same repeating units in the molecule and has such a nature that a more elongated conjugated system results in a higher degree of coloration and also in a greater absorption in the visible region when formed as a charge-transporting thin film.

It is known that the coloration of a charge-transporting thin film lowers the color purity and color reproducibility of an organic electroluminescent (hereinafter referred to as organic EL) device.

In addition, the coloration presents a problem in many full color techniques of organic EL displays such as of tricolor luminescence, white color luminescence, and color conversion and becomes a considerable obstacle in the stable manufacture of organic EL devices.

Therefore, it is desirable that the charge-transporting thin film of an organic EL device be high in transmittance in the visible region and high in transparency.

Patent Document 1: JP-A 2002-151272

DISCLOSURE OF THE INVENTION

Problems to be Solved by the Invention

The present invention has been made under these circumstances in the art and has for its object the provision of an oligoaniline compound capable of providing a charge-transporting thin film wherein coloration in the visible region is suppressed.

Means for Solving the Problems

We made intensive studies in order to achieve the above object and, as a result, found that when using oligoaniline compounds wherein a conjugated system in the molecule is partly severed or an oligoaniline containing as a part thereof a conjugated system constituted of a structure of repeating units other than the aniline unit, there can be obtained a charge-transporting thin film that is suppressed from coloration in the visible region and is excellent in transparency, for which these oligoaniline compounds are useful as a charge transport material capable of satisfactorily developing the function as an organic EL device, thereby accomplishing the invention.

The invention provides:

1. An oligoaniline compound, characterized by being represented by the formula (1)

[Chemical Formula 1]

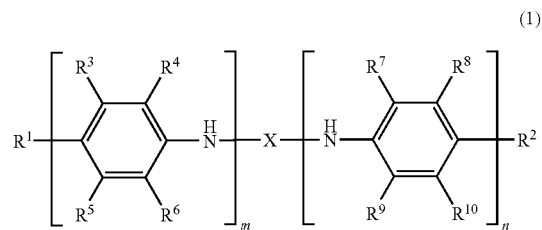

(1)

[wherein $R^1$ to $R^{10}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, m and n are independently an integer of 1 or over provided that m+n=20 is satisfied, and X represents any of groups represented by the following formulas (4) to (21)

[Chemical Formula 2]

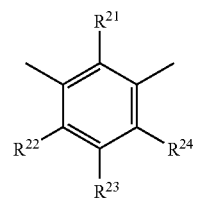

(4)

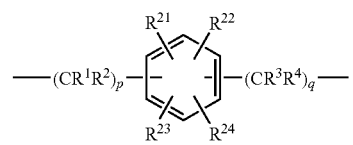

(5)

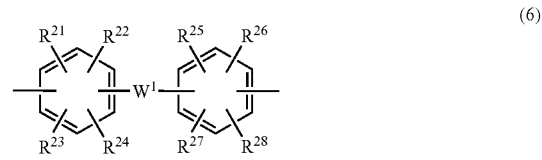

(6)

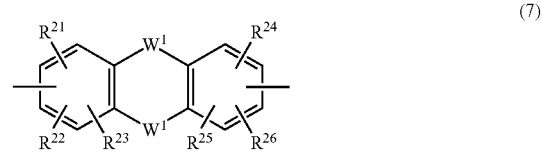

(7)

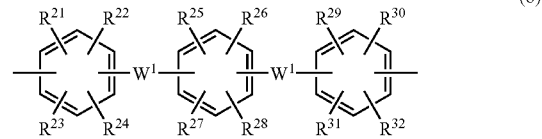

(8)

(9)
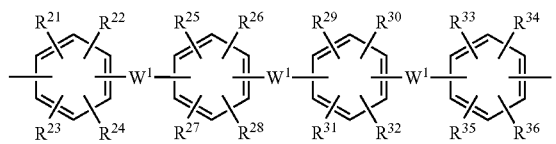

(10)
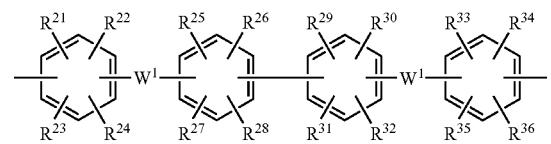

(11)
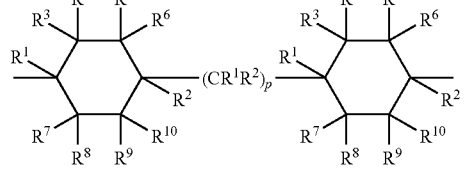

(12)
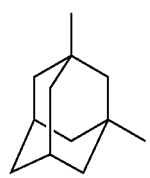

(13)
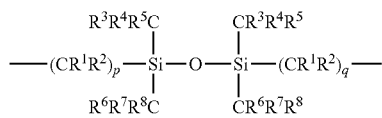

[Chemical Formula 3]

(14)
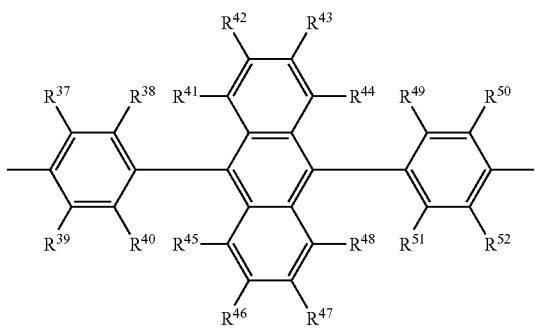

(15)

(16)

(17)

(18)
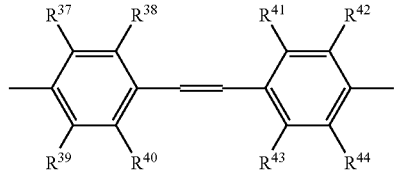

(19)
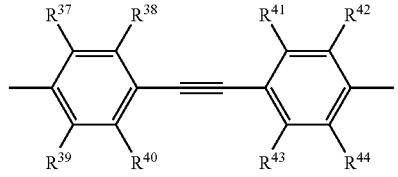

(20)
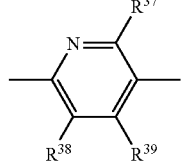

(21)
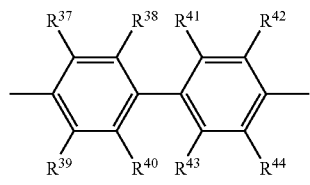

(wherein $R^1$ to $R^{10}$, respectively, have the same meanings as defined above, $R^{21}$ to $R^{52}$ independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, p and q are independently an integer of 1 or over provided that $p \leq 20$ and $q \leq 20$ are satisfied, $W^1$s independently represent —$(CR^1R^2)p$-, —O—, —S—, —S—S—, —$S(O)_2$—, —$NR^1$—, —C(O)—, —C(O)O—, —OC(O)—, —C(S)O—, —OC(S)—, —$C(O)NR^1$—, —$NR^1C(O)$—, —O—$(CR^1R^2)$p-O—, —C(O)O—$(CR^1R^2)$p-OC(O)—, —O—Si$(CR^1R^2)_2$—O— (wherein $R^1$ and $R^2$, respectively, have the same meanings as defined above), a group represented by the following formula (22), or a group represented by the following formula (23))

[Chemical Formula 4]

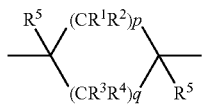
(22)

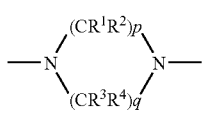
(23)

(wherein $R^1$ to $R^5$, p and q, respectively, have the same meanings as defined above)];

2. An oligoaniline, characterized by being represented by the formula (2)

[Chemical Formula 5]

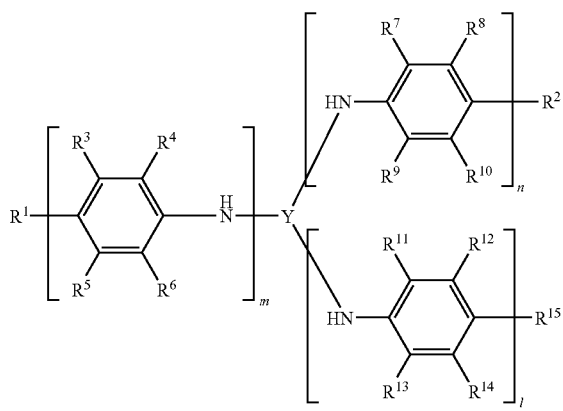
(2)

[wherein $R^1$ to $R^{15}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, m, n and l are independently an integer of 1 or over provided that m+n+l≤20 is satisfied, and Y represents a group represented by the following formula (24) or (25)

[Chemical Formula 6]

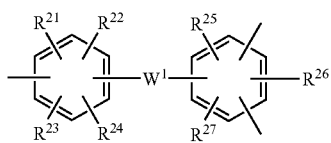
(24)

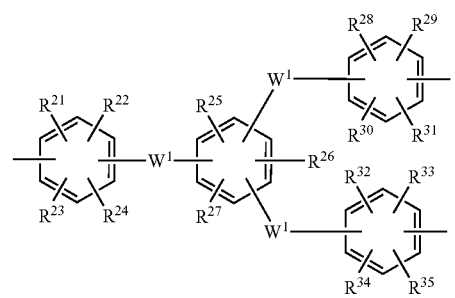
(25)

[wherein $R^{21}$ to $R^{35}$ independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, and $W^1$s independently represent —$(CR^1R^2)$p-, —O—, —S—, —S—S—, —$S(O)_2$—, —$NR^1$—, —C(O)—, —C(O)O—, —OC(O)—, —C(S)O—, —OC(S)—, —$C(O)NR^1$—, —$NR^1C(O)$—, —O—$(CR^1R^2)$p-O—, —C(O)O—$(CR^1R^2)$p-OC(O)—, —O—$Si(CR^1R^2)_2$—O— (wherein $R^1$ and $R^2$, respectively, have the same meanings as defined above), a group represented by the following formula (22), or a group represented by the following formula (23))

[Chemical Formula 7]

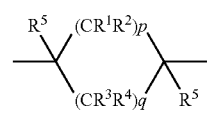
(22)

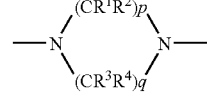
(23)

(wherein $R^1$ to $R^5$, respectively, have the same meanings as defined above, and p and q are, respectively, an integer of 1 or over provide that p≤20 and q≤20)];

3. An oligoaniline compound, characterized by being represented by the formula (3)

[Chemical Formula 8]

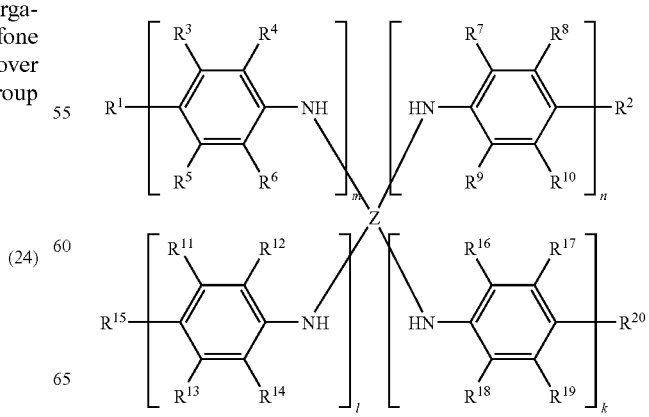
(3)

[wherein $R^1$ to $R^{20}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, m, n, l and k are independently an integer of 1 or over provided that m+n+l+k≤20 is satisfied, and Z represents a group represented by the following formulas (26) or (27).

[Chemical Formula 9]

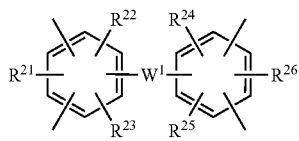
(26)

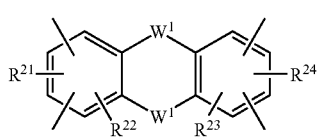
(27)

(wherein $R^{21}$ to $R^{26}$ independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, and $W^1$s independently represent $-(CR^1R^2)p-$, $-O-$, $-S-$, $-S-S-$, $-S(O)_2-$, $-NR^1-$, $-C(O)-$, $-C(O)O-$, $-OC(O)-$, $-C(S)O-$, $-OC(S)-$, $-C(O)NR^1-$, $-O-(CR^1R^2)p-O-$, $-C(O)O-(CR^1R^2)p-OC(O)-$, $-O-Si(CR^1R^2)_2-O-$ (wherein $R^1$ and $R^2$, respectively, have the same meanings as defined above), a group represented by the following formula (22), or a group represented by the following formula (23))

[Chemical Formula 10]

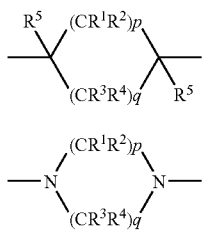
(22)

(23)

(wherein $R^1$ to $R^5$, respectively, have the same meanings as defined above, and p and q are, respectively, an integer of 1 or over provided that p≤20 and q≤20)];
4. The charge transport material made of the oligoaniline compound defined in any of 1 to 3;
5. The charge-transporting varnish including the oligoaniline compound defined in any of 1 to 3;
6. The charge-transporting thin film formed from the charge-transporting varnish of 5;
7. The charge-transporting thin film including the oligoaniline compound defined in any of 1 to 3;
8. The organic electronic device including at least one layer of the charge-transporting thin film of 6 or 7;
9. The organic electroluminescent device including at least one layer of the charge-transporting thin film of 6 or 7; and
10. The organic electroluminescent device of 9, wherein the charge-transporting thin film serves as a hole injection layer or a hole-transporting layer.

Effect of the Invention

Using the oligoaniline compound of the invention, there can be obtained a charge-transporting thin film wherein light absorption in the visible region can be suppressed. The use of this thin film ensures color reproducibility of a device without lowering the color purity of electroluminescent light or light passed through color filters.

The oligoaniline compounds of the invention can be synthesized by amylation of monomers each having a given molecular weight and are obtained as a single compound having no molecular weight distribution. The single compound has an advantage in that it is easier in purification than a series of polymers having individual molecular weight distributions. Since it is required that the charge-transporting thin film of an organic EL device be free of impurities, the thin film formed by use of an oligoaniline compound of the invention which is so easy in purification that impurities can be reduced is favorable as a charge-transporting thin film of an organic EL device.

BRIEF DESCRIPTION OF THE DRAWING

FIG. 1 is a chart showing UV-VIS spectra of thin films obtained from varnishes prepared in Examples 7, 8 and Comparative Example 2.

BEST MODE FOR CARRYING OUT THE INVENTION

The invention is now described in more detail.
In the oligoaniline compounds represented by the formulas (1) to (3), $R^1$ to $R^{20}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group.

The halogen atoms include fluorine, chlorine, bromine and iodine atoms.

The monovalent hydrocarbon groups include: an alkyl group such as a methyl group, an ethyl group, a propyl group, a butyl group, a t-butyl group, a hexyl group, an octyl group, a decyl group or the like; a cycloalkyl group such as a cyclopentyl group, a cyclohexyl group or the like; a bicycloalkyl group such as a bicyclohexyl group or the like; an alkenyl group such as a vinyl group, a 1-propenyl group, a 2-propenyl group, an isopropenyl group, a 1-methyl-2-propenyl group, a 1, 2 or 3-butenyl group, a hexenyl group or the like; an aryl group such as a phenyl group, a xylyl group, a tolyl group, a biphenyl group, a naphthyl group or the like; and an aralkyl group such as a benzyl group, a phenylethyl group, a phenylcyclohexyl group or the like.

It should be noted that part or the whole of hydrogen atoms of these monovalent hydrocarbon groups may be substituted with a hydroxyl group, a halogen atom, an amino group, a silanol group, a thiol group, a carboxyl group, a sulfone group, a phosphate group, a phosphoric acid ester group, an ester group, a thioester group, an amide group, a nitro group, an organoxy group, an organoamino group, an organosilyl group, an organothio group, an acyl group, an alkyl group, a cycloalkyl group, a bicycloalkyl group, an alkenyl group, an aryl group, an aralkyl group or the like.

The organoxy groups include an alkoxy group, an alkenyloxy group, an aryloxy group and the like, in which the alkyl group, alkenyl group and aryl group thereof may be those mentioned with respect to the above monovalent hydrocarbon group.

The organoamino groups include an alkylamino group such as a phenylamino group, a methylamino group, an ethylamino group, a propylamino group, a butylamino group, a pentylamino group, a hexylamino group, a heptylamino group, an octylamino group, a nonylamino group, a decylamino group, a laurylamino group or the like; a dialkylamino group such as a dimethylamino group, a diethylamino group, a dipropylamino group, a dibutylamine group, a dipentylamine group, a dihexylamino group, a diheptylamino group, an dioctylamino group, a dinonylamino group, a didecylamino group or the like; and a cyclohexylamino group, a morpholino group or the like.

The organosilyl groups include a trimethylsilyl group, a triethylsilyl group, a tripropylsilyl group, a tributylsilyl group, a tripentylsilyl group, a trihexylsilyl group, a pentyldimethylsilyl group, a hexyldimethylsilyl group, an octyldimethylsilyl group, a decyldimethylsilyl group and the like.

The organothio groups include alkylthio groups such as a methylthio group, an ethylthio group, a propylthio group, a butylthio group, a pentylthio group, a hexylthio group, a heptylthio group, an octylthio group, a nonylthio group, a decylthio group, a laurylthio group and the like.

The acyl groups include a formyl group, an acetyl group, a propionyl group, a butyryl group, an isobutyryl group, a valeryl group, an isovaleryl group, a benzoyl group and the like.

The phosphoric acid ester groups include —P(O)(OQ$^1$)(OQ$^2$).

The ester groups include —C(O)OQ$^1$ and —OC(O)Q$^1$.
The thioester groups include —C(S)OQ$^1$ and —OC(S)Q$^1$.
The amide groups include —C(O)NHQ$^1$, —NHC(O)Q$^1$, —C(O)NQ$^1$Q$^2$, and —NQ$^1$C(O)Q$^2$.

In the above formulas, Q$^1$ and Q$^2$, respectively, represent an alkyl group, an alkenyl group or an aryl group, and these groups may be similar to those exemplified with respect to the above monovalent hydrocarbon group.

Although the number of carbon atoms in the monovalent hydrocarbon group, organoxy group, organoamino group, organosilyl group, organothio group, acyl group, phosphoric acid ester group, ester group, thioester group, amide group and the like is not critical, the number of carbon atoms generally ranges 1 to 20, preferably 1 to 8.

Of the substituent groups mentioned above, the fluorine atom, sulfone group, substituted or unsubstituted organoxy group, alkyl group and organosilyl group are more preferred.

It should be noted that "unsubstituted" means bonding of a hydrogen atom. In the afore-indicated substituent groups, a cyclic moiety wherein substituent groups are mutually bonded together may be contained.

X in the formula (1) is any of the groups represented by the formulas (4) to (21), Y in the formula (2) is a group represented by the formula (24) or (25), and Z is a group represented by the formula (26) or (28).

R$^{21}$ to R$^{52}$ in the formulas (4) to (21) and (24) to (27) independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, p and q are independently an integer of 1 or over provided that p≤20 and q≤20 are satisfied, W$^1$'s independently represent —(CR$^1$R$^2$)p-, —O—, —S—, —S—S—, —S(O)$_2$—, —NR$^1$—, —C(O)—, —C(O)O—, —OC(O)—, —C(S)O—, —OC(S)—, —C(O)NR$^1$—, —NR$^1$C(O)—, —O—(CR$^1$R$^2$)p-O—, —C(O)O—(CR$^1$R$^2$)p-OC(O)—, —O—Si(CR$^1$R$^2$)$_2$—O— (wherein R$^1$ and R$^2$, respectively, have the same meanings as defined above), a group represented by the foregoing formula (22), or a group represented by the formula (23).

Specific examples of the monovalent hydrocarbon group, organoxy group, organoamino group, organosilyl group, organothio group, acyl group, phosphoric acid ester group, ester group, thioester group and amide group are similar to those illustrated with respect to the R$^1$ to R$^{20}$.

Specific examples of the substituent groups of the formulas (4) to (13) include those indicated below although not limited thereto.

[Chemical Formula 11]

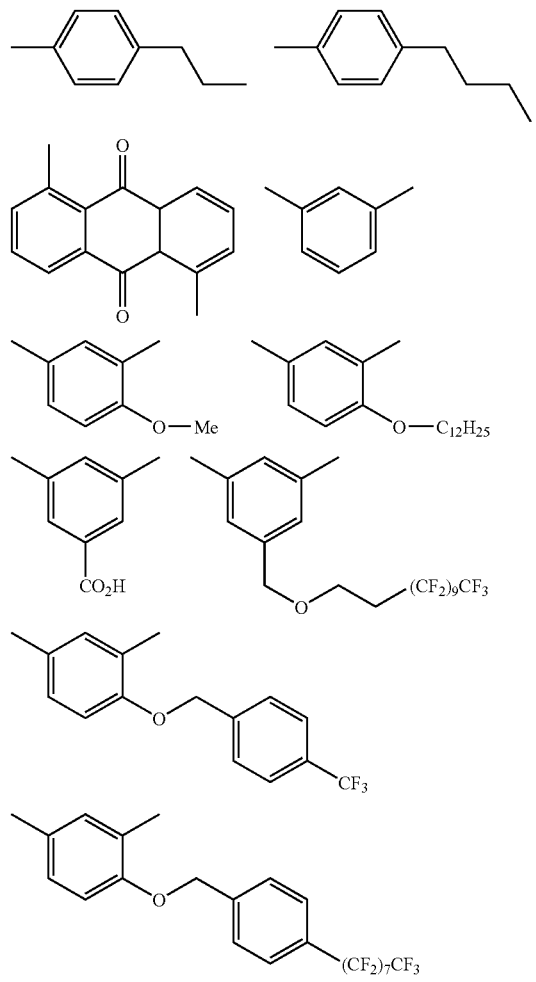

-continued
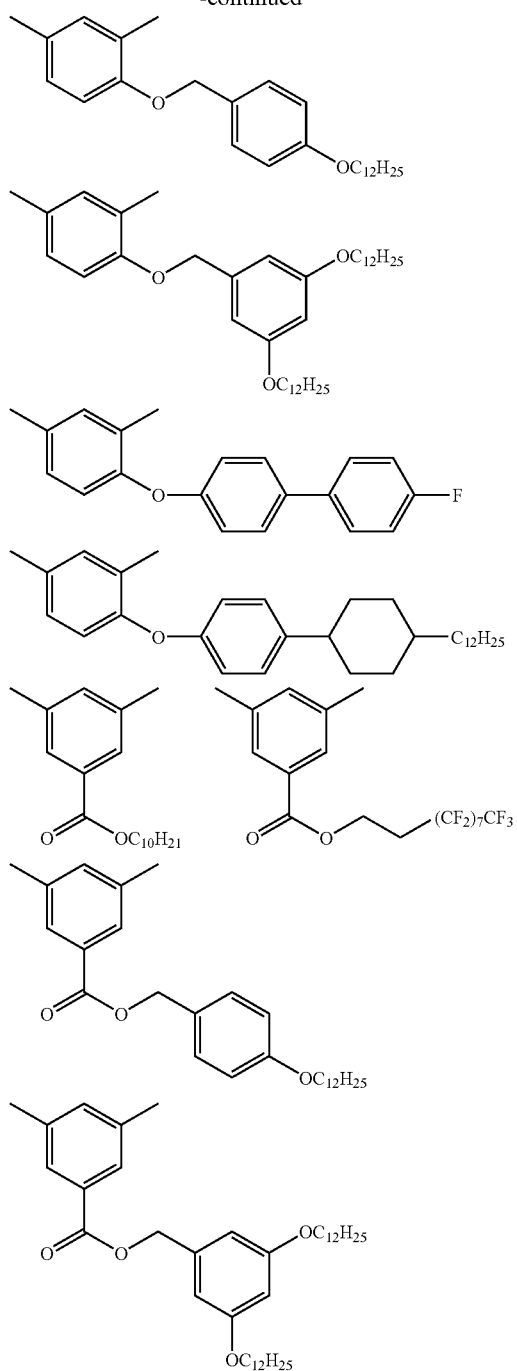
[Chemical Formula 12]
-continued
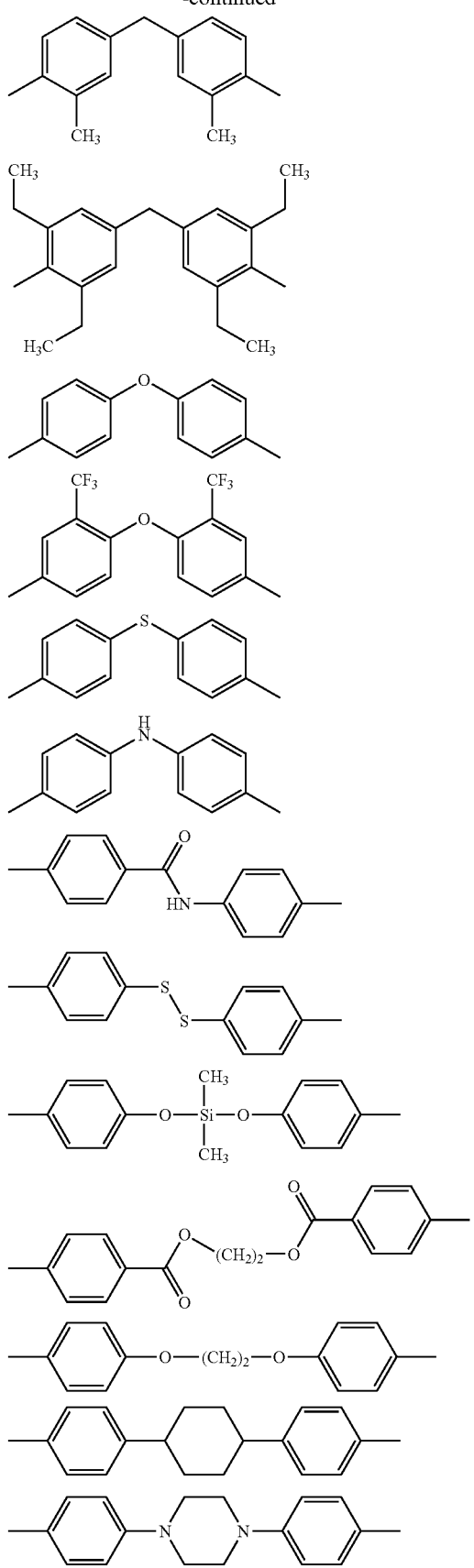

[Chemical Formula 13]
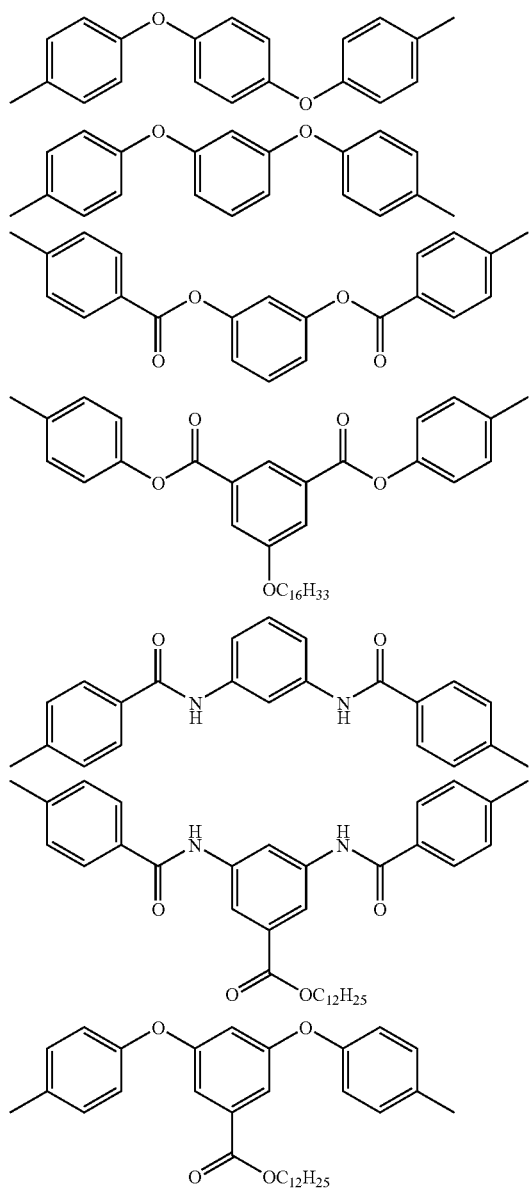
[Chemical Formula 14]
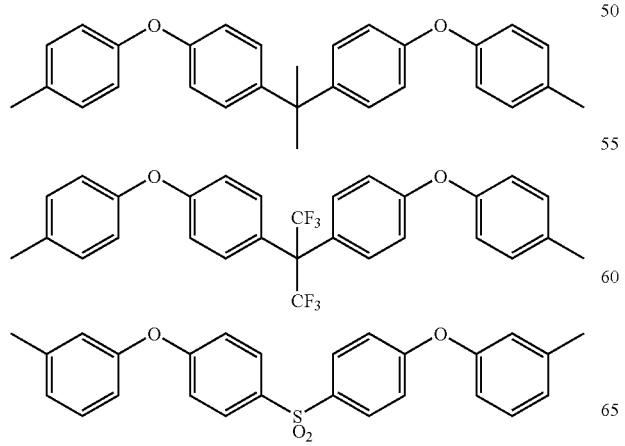
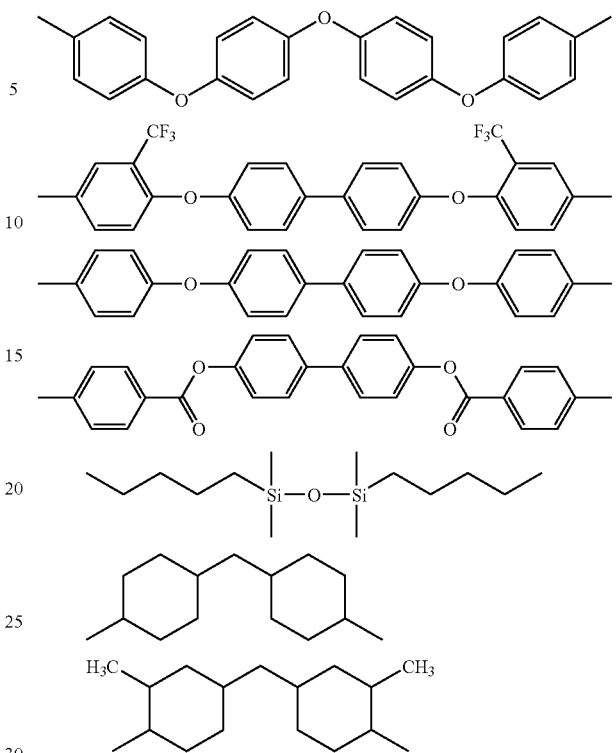
Specific examples of the substituent groups of the formulas (14) to (21) are those indicated below although not limited thereto.
[Chemical Formula 15]
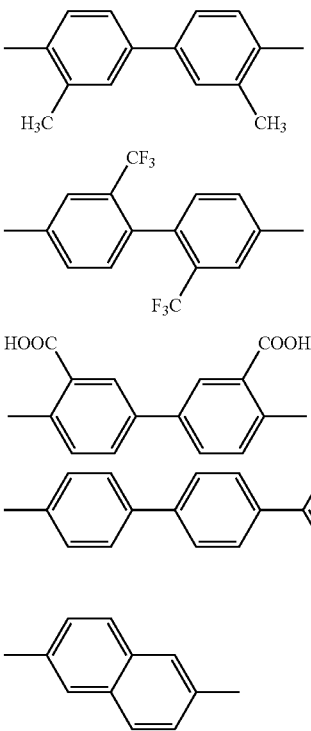

In the oligoaniline compound of the formula (1), m+n is preferably at 4 or over from the standpoint that good charge transportability is shown and is also preferably at 16 or below from the standpoint of ensuring solubility in solvents.

In the oligoaniline compound of the formula (2), m+n+l is preferably at 6 or over from the standpoint that good charge transportability is shown and is preferably at 16 or below from the standpoint of ensuring solubility in solvents.

In the oligoaniline compound of the formula (3), m+n+l+k is preferably at 8 or over from the standpoint that good charge transportability is shown and is preferably at 16 or below from the standpoint of ensuring solubility in solvents.

When taking increased solubility and uniform charge transportability into account, the oligoaniline compounds represented by the formulas (1) to (3) should preferably be those oligoaniline compounds that are free of molecular weight distribution, or have a degree of dispersion of 1. The molecular weight is generally at 200 or over, preferably 400 or over as a lower limit in order to suppress the compound from being volatilized and is generally at 5000 or below, preferably 2000 or below as an upper limit in order to improve solubility.

The oligoaniline compound represented by the formula (1) can be prepared according to the following process although not limited thereto.

More particularly, a p-hydroxydiphenylamine compound and a diamine compound represented by the following formula (28) are reacted in the presence of a titanium tetraalkoxide compound serving as a dehydrating and condensing agent.

[Chemical Formula 18]

$$H_2N-X-NH_2 \qquad (28)$$

The compound to be reacted with the diamine compound of the formula (28) includes, for example, p-hydroxydiphenylamine, 4-[[4-(phenylamino)phenyl]amino]phenol, 4-[[4-[[4-(phenylamino)phenyl]amino]phenyl]amino]phenol, 4-[[4-[[4-[[4-(phenylamino)phenyl]amino]phenyl]amino]phenyl]-amino]phenol, or the like. The amount of these compounds is favorably in the range of 2.0 to 3.0 times by mole relative to the diamine compound of the formula (28).

The tetraalkoxy titanium compounds include titanium tetra-n-methoxide, titanium tetra-n-ethoxide, titanium tetra-n-propoxide, titanium tetra-1-propoxide, titanium tetra-n-butoxide or the like, of which titanium tetra-n-butoxide is preferred. The amount is favorably in the range of 2 to 20 times by mole relative to the diamine compound of the formula (28). It should be noted that n means normal and i means iso.

The reaction solvent includes DMF, DMAc, NMP, DMI, DMSO, THF, 1,4-dioxane, toluene or the like, of which 1,4-dioxane and toluene are preferred.

The reaction temperature may range from −50° C. to a boiling point of a solvent used and is preferably in the range of 80 to 120° C. The reaction time generally ranges 0.1 to 100 hours.

The oligoaniline compounds of the formulas (2) and (3) can be prepared according to the same process of preparing the oligoaniline compound of the formula (1) using the compounds represented by the following formulas (29) and (30), respectively.

[Chemical Formula 19]

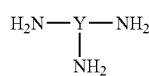
(29)

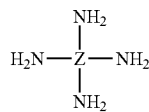
(30)

The oligoaniline compounds of the formulas (1) to (3) obtained according to the above reactions can be purified by a recrystallization method. The recrystallization solvent includes, for example, 1,4-dioxane, tetrahydrofuran or the like although not limited thereto. Particularly, a preferred solvent is one that is unlikely to dissolve an oxidized product of the oligoaniline compound and such a solvent includes, for example, 1,4-dioxane.

The charge-transporting varnish according to the invention includes, as a charge-transporting material, any of the oligoaniline compounds represented by the formulas (1) to (3).

The charge-transporting varnish used herein means a solution or dispersion, in at least one solvent, of a charge-transporting material made of an oligoaniline compound of the invention serving as a charge transport mechanism body, or a charge-transporting organic material made of the charge-transporting material and an electron or hole-accepting dopant material.

It should be noted that charge transportability has the same meaning as electric conductivity and means any of hole transportability, electron transportability and both hole and electron charge transportabilities. The charge-transporting varnish of the invention may have charge transportability in itself, or the solid film obtained from the varnish may have charge transportability.

In order to improve charge transportability and the like of the charge-transporting varnish of the invention, there may be used, as a charge accepting dopant material used if necessary, an electron-accepting dopant material for a hole-transporting material and a hole-accepting dopant material for an electron-transporting material, for which both dopants should preferably have high charge acceptability. With respect to the solubility of the charge-accepting dopant material, no limitation is placed on the type of dopant material so far as those which are soluble in at least one solvent used for the varnish are used.

Specific examples of the charge-accepting dopant material include: inorganic strong acids such as hydrogen chloride, sulfuric acid, nitric acid, phosphoric acid and the like; Lewis acids such as aluminum (III) chloride ($AlCl_3$), titanium (IV) tetrachloride ($TiCl_4$), boron tribromide ($BBr_3$), boron trifluoride ether complex ($BF_3.OEt_2$), iron (III) chloride ($FeCl_3$), copper (II) chloride ($CuCl_2$), antimony (V) pentachloride ($SbCl_5$), arsenic (V) pentafluoride ($AsF_5$), phosphorus pentafluoride ($PF_5$), tris(4-bromophenyl)aluminum hexachloroantimonate (TBPAH) and the like; organic strong acids such as benzenesulfonic acid, tosylic acid, camphorsulfonic acid, hydroxybenzenesulfonic acid, 5-sulfosalicylic acid, dodecylbenzenesulfonic acid, polystyrenesulfonic acid, 1,4-benzodioxanedisulfonic acid derivatives set out in WO 2005/000832, arylsulfonic acid derivatives set out in WO 2006/025342, dinonylnaphthalenesulfonic acid derivatives set out in JP-A 2005-108828 and the like; and organic or inorganic oxidizing agents such as 7,7,8,8-tetracyanoquinodimethane (TCNQ), 2,3-dichloro-5,6-dicyao-1,4-benzoquinone (DDQ), iodine and the like although not limited thereto.

Preferred electron-accepting dopant materials include those dopant materials made of organic strong acids such as 5-sulfosalicyclic acid, dodecylbenzensulfonic acid, polystyrenesulfonic acid, 1,4-benzodioxanedisulfonic acid derivatives set out in WO 2005/000832, dinonylnaphthalenesulfonic acid derivatives set out in JP-A 2005-108828 and the like.

Specific examples of the hole-accepting dopants include alkali metals (Li, Na, K, Cs) and metal complexes such as lithium quinolinolate (Liq), lithium acetylacetonate (Li(a-cac)) and the like although not limited thereto.

As a solvent used for preparing the charge-transporting varnish, there may be used high-solubility solvents capable of well dissolving charge-transporting materials and electron-accepting materials. Examples of such a high-solubility solvent include: water; and organic solvents such as methanol, N,N-dimethylformamide, N,N-dimethyacetamide, N-methylpyrrolidone, 1,3-dimethyl-2-imidazolidinone, dimethylsulfoxide, chloroform, toluene and the like. These solvents may be used singly or in combination of two or more. The amount can be set at 5 to 100 wt % relative to the total of solvents used for the varnish.

It should be noted that the charge-transporting varnish should preferably be in a state of being fully dissolved or uniformly dispersed in the above-mentioned solvent.

The charge-transporting varnish of the invention has a viscosity of 10 to 200 mPa·s, preferably 50 to 150 mPa·s at 20° C., and should favorably contain at least one high-viscosity organic solvent having a boiling point of 50 to 300° C., preferably 150 to 250° C. at normal pressures.

The high-viscosity organic solvents are not critical in type and include, for example, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol, hexylene glycol and the like.

The amount of the high-viscosity solvent relative to the total of solvents used in the varnish of the invention should preferably be within a range where no solid matter precipitates and in so far as no solid matter precipitates, the amount is preferably in the range of 5 to 80 wt %.

Further, for the purposes of improving wettability against a substrate and controlling the surface tension, polarity and boiling point of solvents, other type of solvent capable of imparting flatness to a film upon baking may be mixed in an amount of 1 to 90 wt %, preferably 1 to 50 wt %, relative to the total of solvents used in the varnish.

Such solvents include, for example, butyl cellosolve, diethylene glycol diethyl ether, dipropylene glycol monomethyl ether, ethyl carbitol, diacetone alcohol, γ-butyrolactone, ethyl lactate and the like although not limited thereto.

Such a charge-transporting varnish as illustrated above is coated onto a substrate and the solvent is evaporated to form a charge-transporting thin film on the substrate.

The coating method of the varnish is not critical and includes, for example, a dipping method, a spin coating method, a transfer printing method, a roll coating method, a brushing method, an ink jet method, a spraying method and the like.

The manner of evaporating a solvent is not critical and the solvent may be evaporated, for example, by use of a hot plate or oven in an appropriate atmosphere such as of air, an inert gas such as nitrogen or the like, or in vacuum. In this way, a thin film having a uniform film-formed surface can be obtained.

The baking temperature is not critical so far as a solvent can be evaporated and is preferably at 40 to 250° C. In this case, for the purposes of ensuring more uniform film-forming properties and permitting the reaction to proceed on a substrate, the temperature may be changed in two or more steps.

The thickness of the charge-transporting thin film is not critical. Where the thin film is used as a charge injection layer of an organic EL device, the thickness preferably ranges 5 to 200 nm. For changing the film thickness, a solid content in the varnish may be changed, or an amount of a coating solution on a substrate may be changed.

In case where an OLED device is made using the charge-transporting varnish of the invention, the materials and making method used therefor are those set out below although not limited thereto.

The electrode substrate used is preferably cleaned by preliminarily cleaning with a liquid such as pure water or the like. For instance, with an anode substrate, it is preferred to subject the substrate to surface treatment, such as an ozone treatment, an oxygen-plasma treatment or the like immediately before use. If an anode material is made primarily of an organic matter, no surface treatment may be carried.

Where a hole-transporting varnish is used in an OLED device, the following procedure may be adopted.

The hole-transporting varnish is coated onto an anode substrate, followed by evaporating and baking in a manner as set out above to form a hole-transporting thin film on the electrode. This is introduced into a vacuum deposition apparatus, followed by successive vacuum deposition of a hole-transporting layer, emission layer, electron-transporting layer, electron injection layer and cathode metal to provide an OLED device. For controlling a light-emitting region, a carrier block layer may be provided between arbitrary adjacent layers.

The anode material includes a transparent electrode material typical of which is indium tin oxide (ITO) or indium zinc oxide (IZO), and a flattened electrode is preferred. Polythiophene derivatives and polyaniline derivatives having high charge transportability may also be used.

The materials used to form the hole-transporting layer include triarylamines such as (triphenylamine)dimer derivative (TPD), (α-naphthyldiphenylamine)dimer (α-NPD), [(triphenylamine)dimer]spirodimer (Spiro-TAD) and the like, star burst amines such as 4,4',4''-tris[3-methylphenyl(phenyl)amino]triphenylamine (m-MTDATA), 4,4',4''-tris[1-naphthyl(phenyl)amino]triphenylamine (1-TNATA) and the like, and oligothiophenes such as 5,5''-bis-{4-[bis(4-methylphenyl)amino]phenyl}-2,2':5',2''-terthiophene (BMA-3T) and the like.

The materials for forming the emission layer include tris(8-quinolinolato)aluminum (III) ($Alq_3$), bis(8-quinolinolato) zinc (II) ($Znq_2$), bis(2-methyl-8-quinolinolato)(p-phenylphenolato)aluminum (III) (BAlq), 4,4'-bis(2,2-diphenylvinyl) biphenyl (DPVBi) and the like. The emission layer may be formed by co-deposition of an electron-transporting material or hole-transporting material and a light-emitting dopant.

The electron-transporting materials include $Alq_a$, BAlq, DPVBi, (2-(4-biphenyl)-5-(4-t-butylphenyl)-1,3,4-oxadiazole (PBD), a triazole derivative (TAZ), bathocuproine (BCP), a silole derivative and the like.

The light-emitting dopant includes quinacridone, rubrene, coumarin 540, 4-(dicyanomethylene)-2-methyl-6-(p-dimethylaminostyryl)-4H-pyran (DCM), tris(2-phenylpyridine)-iridium (III) ($Ir(ppy)_3$), (1,10-phenthroline)-tris(4,4,4-trifluoro-1-(2-thienyl)-butan-1,3-dionate)europium (III) (Eu $(TTA)_3$phen) and the like.

The materials for forming the carrier block layer include PBZ, TAZ, BCP and the like.

The materials for forming the electron injection layer include lithium oxide ($Li_2O$), magnesium oxide (MgO), alumina ($Al_2O_3$), lithium fluoride (LiF), magnesium fluoride ($MgF_3$), strontium fluoride ($SrF_2$), Liq, Li(acac), lithium acetate, lithium benzoate and the like.

The cathode materials include aluminum, magnesium-silver alloy, aluminum-lithium alloy, lithium, sodium, potassium, cesium and the like.

Where the electron-transporting varnish is used for an OLED device, the following method can be used.

The electron-transporting varnish is coated onto a cathode substrate to form an electron-transporting thin film, and the film is introduced into a vacuum deposition apparatus, followed by forming an electron-transporting layer, an emission layer, a hole-transporting layer and a hole injection layer by use of such materials as mentioned hereinabove and forming a film of an anode material by a method such as of sputtering to provide an OLED device.

Although a method of making a PLED device by use of the charge-transporting varnish of the invention is not critical, the following method can be mentioned.

In the fabrication of the above-stated OLED device, a light-emitting charge-transporting polymer layer is formed in place of carrying out the vacuum deposition operations of the hole-transporting layer, emission layer, electron-transporting layer and electron injection layer, there by providing a PLED device including a charge-transporting thin film formed with the charge-transporting varnish of the invention.

More particularly, the charge-transporting varnish (hole-transporting varnish) is coated onto an anode substrate to form a hole-transporting thin film according to such a method as set out hereinabove, on which a light-emitting charge-transporting polymer layer is formed, followed by vacuum deposition of a cathode electrode to provide a PLED device.

Alternatively, a charge-transporting varnish (electron-transporting varnish) is coated onto a cathode substrate to form an electron-transporting thin film according to such a method as set out above, on which a light-emitting charge-transporting polymer layer is formed, followed by further formation of an anode electrode by a method such as of sputtering, vacuum deposition, spin coating or the like to provide a PLED device.

The cathode and anode materials used are similar to those used for the fabrication of the OLED device and may be subjected to similar cleaning treatment and surface treatment.

For the formation of the light-emitting charge-transporting polymer layer, mention is made of a method wherein a light-emitting charge-transporting polymer material or this polymer material to which a light-emitting dopant is added is dissolved or uniformly dispersed in a solvent added thereto, followed by coating onto an electrode substrate on which a hole injection layer has been formed, followed by evaporation of the solvent for film formation.

The light-emitting charge-transporting polymer materials include polyfluorene derivatives such as poly(9,9-dialkylfluorene)(PDAF) and the like, polyphenylenevinylene derivatives such as poly(2-methoxy-5-(2'-ethylhexoxy)-1,4-phenylenevinylene) (MEH-PPV) and the like, polythiophene derivatives such as poly(3-alkylthiophene) (PAT) and the like, polyvinylcarbazole derivatives (PVCz), and the like.

The solvents include toluene, xylene, chloroform and the like. The method of the dissolution or uniform dispersion includes a stirring method, a thermal stirring method, a supersonic dispersion method or the like.

The coating method is not critical and includes an ink jet method, a spraying method, a dipping method, a spin coating method, a transfer printing method, a roll coating method, a brushing method or the like. It should be noted that the coating is preferably carried out in an inert gas such as nitrogen, argon or the like.

The evaporation of solvent is carried out by a method of heating in an oven or on a hot plate in an inert gas or in vacuum.

EXAMPLES

Examples and Comparative Examples are described to more particularly illustrate the invention and the following Examples should not be construed as limiting the invention thereto. It is to be noted that measuring apparatuses used in the Examples are indicated below.

[MS Spectrum]
Apparatus (MALDI-TOF):
Voyager-DE™, made by Applied Biosystems Japan PRO.
Apparatus (FAB): JMS-700T, made by JEOL Ltd.

[NMR Spectrum]
ECP300, made by JEOL Ltd.

[Elementary Analysis]
PE2400 series II, made by Perkin Elmer Co., Ltd.

[1] Synthesis of Oligoaniline Compound

Comparative Example 1

Phenyltetraaniline (hereinafter abbreviated as PTA) represented by the formula (31) was synthesized from p-hydroxydiphenylamine and p-phenylenediamine according to the method described in Bulletin of Chemical Society of Japan, 1994, Vol. 67, pp. 1749-1752. (light blue solid, yield of 85%)

[Chemical Formula 20]

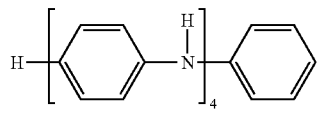

Under nitrogen atmosphere, 20 g (0.0452 mmols) of the resulting PTA, 2 g of active carbon (10 wt % of PTA) and 500 g of dehydrated 1,4-dioxane that had been degassed by use of ultrasonic waves were added to a one liter three-necked round bottom flask. Next, while keeping the internal temperature at 90° C. by use of an oil bath, the content was heated under stirring for 1 hour to completely dissolve PTA. Thereafter, using Kiriyama glass S-60, Kiriyama paper filter 3C and Celite 545 as a stationary phase, thermal filtration was carried out while keeping a temperature controller-equipped water circulator at 90° C., thereby removing the active carbon. The resulting filtrate was allowed to cool until the internal temperature reached 20° C. After the cooling, a light purple solution wherein PTA precipitated was moved in a glove box while being placed in the reaction container wherein nitrogen flow was performed until the relative humidity arrived at 5%. While keeping the relative humidity at 5%, the precipitated PTA was subjected to suction filtration in the glove box. The PTA in the Büchner funnel was washed with 200 ml of 1,4-dioxane, 200 ml of dehydrated toluene and 200 ml of diethyl ether in this order. The PTA was moved to a 100 ml round bottom flask in the glove box by use of a fluorine resin microspartel, followed by pressure reduction by use of a three-way stopcock and purging with nitrogen. Subsequently, the content was dried for 24 hours under a reduced pressure in a vacuum dryer kept at 120° C. to obtain 19.34 g of white solid PTA. The recovery rate was 96%.

It should be noted that dehydrate 1,4-dioxane was one made by Kanto Chemical Co., Inc., hydrazine monohydrate was one made by Wako Pure Chemical Industries, Ltd., active carbon was one made by Junsei Chemical Co., Ltd., and Celite is one made by Junsei Chemical Co, Ltd.

Example 1

Bis(4-diphenylamino)-4,4'-diaminodiphenylmethane (hereinafter abbreviated as BDDM) represented by the formula (32) was prepared from p-hydroxydiphenylamine and 4,4'-diaminodiphenylmethane according to the following procedure (white solid, yield of 60%).

[Chemical Formula 21]

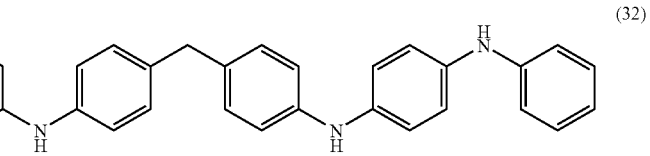

In 1 liter of toluene, 9.913 g (0.05 mols) of 4,4'-diaminodiphenylmethane was dissolved. To obtain a dehydrating condensation agent, 153.144 g (0.45 mols) of titanium tetra-n-butoxide and 67.5765 g (0.45 mols) of p-tolyl acetate were evaporated on a water bath of 60° C. for 60 minutes to completely distill off the resulting butyl acetate. This agent was added to the solution.

While keeping the reaction solution at 110° C., 22.2264 g (0.12 mols) of p-hydroxydiphenylamine was added to the solution under nitrogen atmosphere, followed by reaction at the temperature for 48 hours under nitrogen atmosphere. After completion of the reaction, the reaction solution, cooled down to room temperature, was filtered and the resulting filtrate was washed with toluene and then with diethyl ether and dried to obtain white powder.

The thus obtained crude product of BDDM was purified according to the treatment with active carbon and recrystallization treatment as in Comparative Example 1. The recovery rate was at 95%.

Example 2

Bis(4-diphenylamino)-4,4'-diaminodiphenyl ether (hereinafter abbreviated as BDDE) represented by the formula (33) was prepared from p-hydroxydiphenylamine and 4,4'-diaminodiphenyl ether according to the following procedure (white solid, yield of 89%).

[Chemical Formula 22]

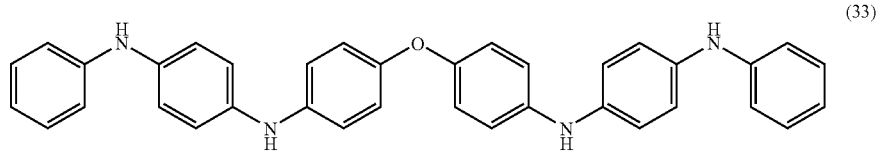

In 1 liter of toluene, 10.012 g (0.05 mols) of 4,4'-diaminodiphenylether was dissolved. To obtain a dehydrating condensation agent, 153.144 g (0.45 mols) of titanium tetra-n-butoxide and 67.5765 g (0.45 mols) of p-tolyl acetate were evaporated on a water bath of 60° C. for 60 minutes to completely distill off the resulting butyl acetate. This agent was added to the solution.

While keeping the reaction solution at 110° C., 22.2264 g (0.12 mols) of p-hydroxydiphenylamine was added to the solution under nitrogen atmosphere, followed by reaction at the temperature for 48 hours under nitrogen atmosphere. After completion of the reaction, the reaction solution, cooled down to room temperature, was filtered and the resulting filtrate was washed with toluene and then with diethyl ether and dried to obtain white powder.

The thus obtained crude product of BDDE was purified according to the treatment with active carbon and recrystallization treatment as in Comparative Example 1. The recovery rate was at 94%.

Example 3

Bis(4-diphenylamino)-2,2'-dimethyl-4,4'-diaminobiphenyl (hereinafter abbreviated as BDDMD) represented by the formula (34) was prepared from p-hydroxydiphenylamine and 2,2'-dimethylbenzidine according to the following procedure (white solid, yield of 88%).

[Chemical Formula 23]

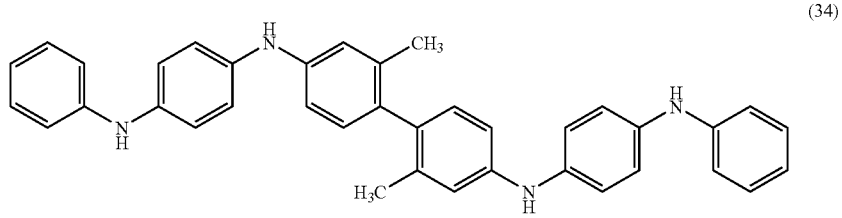

(34)

In 1 liter of toluene, 10.6145 g (0.05 mols) of 2,2'-dimethylbenzidine was dissolved. To obtain a dehydrating condensation agent, 153.144 g (0.45 mols) of titanium tetra-n-butoxide and 67.5765 g (0.45 mols) of p-tolyl acetate were evaporated on a water bath of 60° C. for 60 minutes to completely distill off the resulting butyl acetate. This agent was added to the solution.

While keeping the reaction solution at 110° C., 22.2264 g (0.12 mols) of p-hydroxydiphenylamine was added to the solution under nitrogen atmosphere, followed by reaction at the temperature for 48 hours under nitrogen atmosphere. After completion of the reaction, the reaction solution, cooled down to room temperature, was filtered and the resulting filtrate was washed with toluene and then with diethyl ether and dried to obtain white powder.

The thus obtained crude product of BDDMD was purified according to the treatment with active carbon and recrystallization treatment as in Comparative Example 1. The recovery rate was at 98%.

Example 4

Bis(4-diphenylamino)-4,4'-diaminodiphenylsulfide (hereinafter as BDDS) represented by the formula (35) was prepared from p-hydroxydiphenylamine and 4,4'-diaminodiphenylsulfide according to the following procedure (white solid, yield of 90%).

[Chemical Formula 24]

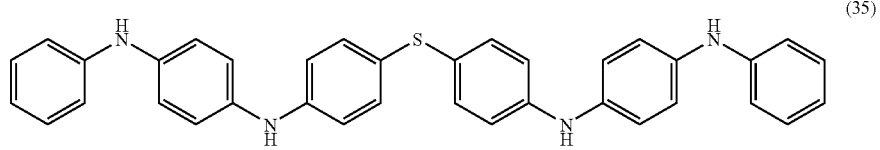

(35)

In 1 liter of toluene, 10.8150 g (0.05 mols) of 4,4'-diaminodiphenylsulfide was dissolved. To obtain a dehydrating condensation agent, 153.144 g (0.45 mols) of titanium tetra-n-butoxide and 67.5765 g (0.45 mols) of p-tolyl acetate were evaporated on a water bath of 60° C. for 60 minutes to completely distill off the resulting butyl acetate. This agent was added to the solution.

While keeping the reaction solution at 110° C., 22.2264 g (0.12 mols) of p-hydroxydiphenylamine was added to the solution under nitrogen atmosphere, followed by reaction at the temperature for 48 hours under nitrogen atmosphere. After completion of the reaction, the reaction solution, cooled down to room temperature, was filtered and the resulting filtrate was washed with toluene and then with diethyl ether and dried to obtain white powder.

The thus obtained crude product of BDDS was purified according to the treatment with active carbon and recrystallization treatment as in Comparative Example 1. The recovery rate was at 95%.

The structures of the oligoaniline compounds represented by the formulas (31) to (35) were, respectively, identified by $^1$H-NMR, MALDI-TOF-MS and elementary analyses. The results of the MALDI-TOF-MS and elementary analyses are shown in Table 1, and the results of $^1$H-NMR are shown in Table 2.

TABLE 1

| Entry | Abbreviation | Compositional formula | Molecular weight [g/mol] | MALDI-TOF-MS [m/z] | Elementary analysis [%] |
|---|---|---|---|---|---|
| Comparative Example 1 | PTA | $C_{30}H_{26}N_4$ | 442.55 | 442.43 | Calcd.: C, 81.41; H, 5.92; N, 12.66 Found: C, 81.51; H, 5.80; N, 12.54 |
| Example 1 | BDDM | $C_{37}H_{32}N_4$ | 532.68 | 531.99 | Calcd.: C, 83.43; H, 6.06; N, 10.52 Found: C, 83.63; H, 6.17; N, 10.46 |
| Example 2 | BDDE | $C_{36}H_{30}N_4O$ | 534.65 | 533.94 | Calcd.: C, 80.87; H, 5.66; N, 10.48 Found: C, 80.05; H, 5.71; N, 10.17 |
| Example 3 | BDDMD | $C_{38}H_{34}N_4$ | 535.70 | 535.93 | Calcd.: C, 83.48; H, 6.27; N, 10.25 Found: C, 83.49; H, 6.06; N, 10.00 |
| Example 4 | BDDS | $C_{36}H_{30}N_4S$ | 550.72 | 550.02 | Calcd.: C, 78.51; H, 5.49; N, 10.17; S, 5.82 Found: C, 78.44; H, 5.44; N, 10.10; S, 5.65 |

TABLE 2

| Entry | $^1$H-NMR [ppm] |
|---|---|
| Comparative Example 1 | 7.75 (s, NH × 2, 2H), 7.60 (s, NH × 2, 2H), 7.14 (dd, J = 7.2, 7.5, Arom., m-2H × 2, 4H), 7.01-6.87 (m, Arom., o-2H × 8, 16H), 6.69 (dd, J = 7.5, 7.5, Arom., p-H × 2, 2H) |
| Example 1 | 7.85 (s, NH × 2, 2H), 7.80 (s, NH × 2, 2H), 7.15 (dd, J = 8.4, 7.5, Arom., m-2H × 2, 4H), 7.04-6.89 (m, Arom., o-2H × 10, 20H), 6.70 (dd, J = 7.5, 7.2, Arom., p-H × 2, 2H), 3.72 (s, —CH$_2$, 2H) |
| Example 2 | 7.85 (s, NH × 2, 2H), 7.81 (s, NH × 2, 2H), 7.16 (dd, J = 7.2, 7.5, Arom., m-2H × 2, 4H), 7.04-6.85 (m, Arom., o-2H × 10, 20H), 6.68 (dd, J = 7.5, 7.2, Arom., p-H × 2, 2H) |
| Example 3 | 7.87 (s, NH × 2, 2H), 7.83 (s, NH × 2, 2H), 7.18 (dd, J = 7.8, 7.8, Arom., 2H × 2.4H), 7.06 (s, Arom., 2H × 4, 8H), 6.96 (d, J = 7.8, Arom., 2H × 2.4H), 6.88-6.81 (m, Arom., 2H × 3.6H), 6.72 (dd, J = 7.5, 7.2, Arom., H × 2, 2H), 1.97 (s, —CH$_3$ × 2.6H) |
| Example 4 | 8.08 (s, NH × 2, 2H), 7.93 (s, NH × 2, 2H), 7.17 (dd, J = 8.1, 8.1, Arom., m-2H × 2, 4H), 7.03-6.90 (m, Arom., o-2H × 10, 20H), 6.73 (dd, J = 6.9, 7.5, Arom., p-H × 2, 2H) |

[Measurement of Lightness of the Oligoaniline Compounds (Solid State)]

The lightness (hereinafter abbreviated as L*) in the solid state of the respective oligoaniline compounds obtained in Examples 1 to 4 and Comparative Example 1 was measured according to the following procedure.

About 10 g of the oligoaniline compound was weighed and milled for about 5 minutes by use of a mortar until solid lumps were not visually observed. The milled solid was placed in a glass cell (with a radius of 4 cm and a depth of 1.5 cm) so that the depth of the solid was at about 1 cm. The measuring conditions of a colorimeter were such that a first light source used was a C light source, a visual field was at 2°, a measuring method was CREELP (reflection measurement, removal of specular reflected light, maximum measuring diameter and petri dish selected as a target mask), and the measurement was made once. The measurement was invariably carried out through the target mask on a measuring instrument. After zero calibration, box correction and white plate correction with a guaranteed value of L*=96 to 99, a white plate was taken as a reference value, under which the respective solids were measured. It should be noted that L* was measured by use of Spectrophotometer CM-3500d, made by Konica Minolta Holdings, Inc.

The results are shown in Table 3.

TABLE 3

|  | L* |
|---|---|
| Comparative Example 1 | 84.29 |
| Example 1 | 87.54 |
| Example 2 | 87.19 |
| Example 3 | 86.88 |
| Example 4 | 86.79 |

As shown in Table 3, L* in the solid state of the oligoaniline compounds of Examples 1 to 4 wherein a different structure was introduced into the repeating units is higher than that of PTA. It should be noted that L* indicates white color when it is closer to 100 and black color as being closer to 0.

[2] Fabrication of Charge-Transporting Varnishes and Charge-Transporting Thin Films Comparative Example 2

Under nitrogen atmosphere, 0.0500 g (0.1130 mmols) of PTA obtained in Comparative Example 1, and 0.1149 g (0.4520 mols, calculated as SSA) of 5-sulfosalucyclic acid (hereinafter abbreviated as 5-SSA dihydrate) were completely dissolved in 0.8433 g of N,N-dimethylacetamide (hereinafter abbreviated as DMAc). To the resulting solution, 2.5299 g of cyclohexanol (hereinafter abbreviated as c-HexOH) was added and stirred to prepare a charge-transporting varnish (solid content of 4.2%).

This charge-transporting varnish was used to form a hole-transporting thin film on an ITO-attached glass substrate by a spin coating method in the following way.

The ITO-attached glass substrate was subjected to ozone cleaning for 40 minutes immediately before the spin coating of the varnish. The varnish was coated onto the substrate by spin coating and baked in air at 200° C. for 60 minutes to provide a uniform thin film.

[Chemical Formula 25]

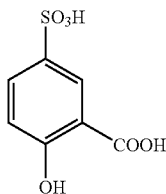

(36)

Example 5

Under nitrogen atmosphere, 0.0602 g (0.1130 mmols) of BDDM obtained in Example 1 and 0.1149 g (0.4520 mmols, calculated as SSA) of 5-SSA dihydrate were completely dissolved in 0.9015 g of DMAc. To the resulting solution, 2.7044 g of c-HexOH was added and stirred to prepare a charge-transporting varnish (solid content of 4.2%).

In the same manner as in Comparative Example 2 except that this charge-transporting varnish was used, there was formed a hole-transporting thin film on an ITO-attached glass substrate.

Example 6

Under nitrogen atmosphere, 0.0604 g (0.1130 mmols) of BDDE obtained in Example 2 and 0.0575 g (0.2260 mmols, calculated as SSA) of 5-SSA dihydrate were completely dissolved in 0.6237 g of DMAc. To the resulting solution, 1.8710 g of c-HexOH was added and stirred to prepare a charge-transporting varnish (solid content of 4.2%).

In the same manner as in Comparative Example 2 except that this charge-transporting varnish was used, there was formed a hole-transporting thin film on an ITO-attached glass substrate.

Example 7

Under nitrogen atmosphere, 0.0605 g (0.1130 mmols) of BDDMD obtained in Example 3 and 0.0575 g (0.2260 mmols, calculated as SSA) 5-SSA dihydrate were completely dissolved in 0.6243 g of DMAc. To the resulting solution, 1.8730 g of c-HexOH was added and stirred to prepare a charge-transporting varnish (solid content of 4.2%).

In the same manner as in Comparative Example 2 except that this charge-transporting varnish was used, there was formed a hole-transporting thin film on an ITO-attached glass substrate.

Example 8

Under nitrogen atmosphere, 0.0622 g (0.1130 mmols) of BDDS obtained in Example 4 and 0.1149 g (0.4520 mmols, calculated as SSA) of 5-SSA dihydrate were completely dissolved in 0.9131 g of DMAc. To the resulting solution, 2.7394 g of c-HexOH was added and stirred to prepare a charge-transporting varnish (solid content of 4.2%).

In the same manner as in Comparative Example 2 except that this charge-transporting varnish was used, there was formed a hole-transporting thin film on an ITO-attached glass substrate.

The thickness, electric conductivity and ionization potential (hereinafter abbreviated as Ip) of the thin films obtained in Examples 5 to 8 and Comparative Example 2 are shown in Table 4.

The thickness was measured by surface profile measuring apparatus DEKTAK 3ST, made by Ulvac Inc, and Ip was measured by use of a photoelectronic spectrometer AC-2, made by Riken Keiki Co., Ltd.

The electric conductivity was measured by introducing the substrates formed thereon with the films in Examples 5 to 8 and Comparative Example 2 into a vacuum deposition apparatus, and vacuum-depositing Al on each hole-transporting thin film in a thickness of 100 nm at a pressure of $8 \times 10^{-1}$ Pa or below at a deposition rate of 0.3 to 0.4 nm/second so that ITO was provided as an anode and the Al provided as a cathode. The electric conductivity was indicated as a value in case where 100 mA/cm² is provided as a threshold.

It should be noted that the respective varnishes of Examples 5 to 8 and Comparative Example 2 were such that the acceptor (5-SSA) was added in an amount of 2 or 4 equivalents relative to the host (charge-transporting material). This number of equivalents adopted was one that became greatest when a varnish was formed as a film on the ITO in a thickness of 30 nm by spin coating, followed by measurement of electric conductivity according to the above procedure.

TABLE 4

| | Equivalents of 5-SSA (eq.) | Film thickness (nm) | Conductivity (S/cm) | Ip (eV) |
|---|---|---|---|---|
| Comparative Example 2 | 4 | 30 | $6.36 \times 10^{-7}$ | 5.34 |
| Example 5 | 4 | 30 | $4.11 \times 10^{-7}$ | 5.31 |
| Example 6 | 2 | 30 | $2.55 \times 10^{-7}$ | 5.44 |
| Example 7 | 2 | 30 | $2.11 \times 10^{-7}$ | 5.41 |
| Example 8 | 4 | 30 | $6.41 \times 10^{-7}$ | 5.35 |

As shown in Table 4, the conductivities of all the materials were on the order of $10^{-7}$ S/cm, revealing that BDDM, BDDE, BDDM and BDDS having a conjugated system partially cut off in the molecule or having a conjugated system constituted of different types of repeating unit structures have the same conductivity as PTA wherein the conjugated system is elongated throughout the molecule.

Although it is assumed that a compound of the type wherein a different structure is introduced into repeating units lowers in conductivity because the conjugated system of π electrons is generally cut off, similar conductivity is obtained as shown above. This is considered for the reason that the conductive materials are small in molecule size and low in molecular weight. Polyaniline having a long molecular chain has a main electric conduction mechanism in the molecule, whereas it is suggested that the main electric conduction mechanism of an oligoaniline having a short molecular chain results from hopping between molecules. Accordingly, it is assumed that if the conjugated system is cut off in the molecule, there is not so much influence on the electric conductivity of the thin film.

[Measurement of Lightness of Oligoaniline Compounds (in a Varnish State)]

L* of the varnishes in the form of a solution prepared in Examples 5 to 8 and Comparative Example 2 was measured according to the following procedure.

A varnish (2.5 ml) was placed in a glass cell (light path length: 2.0 mm). The measurement was made under such measuring conditions of a colorimeter that a first light source was a D light source, a view angle was at 2°, a measuring method was CTIELL (transmission measurement, specular reflection light contained, measured diameter being maximum, and target mask selected as maximum), and the number of measurement was one. The measurement was invariably made through the target mask above a measuring instrument. After correction with a light-shielding plate and correction with a cell to which only a solvent for the varnish (DMAc:c-HexOH=1:3) was added, the respective varnishes were subjected to the measurement. The measuring instrument was the same as mentioned above.

The results are shown in Table 5.

TABLE 5

|  | L* |
|---|---|
| Comparative Example 2 | 95.63 |
| Example 5 | 99.19 |
| Example 6 | 98.85 |
| Example 7 | 98.26 |
| Example 8 | 98.16 |

As shown in Table 5, L*s of the charge-transporting varnishes of Examples 5 to 8 making use of the oligoaniline compounds wherein a different structure is introduced into repeating units are higher than that of PTA. With the solution systems, although the results of the measurement are in such a doped state of an acceptor being added, the degree of coloration of the solid per se shown in Table 3 is reflected, with the result that it will be seen that the coloration of the solution can be suppressed.

[UV to Visible Light Transmission (Hereinafter Abbreviated as UV-VIS) Spectrum Measurement]

The varnishes prepared in Examples 7, 8 and Comparative Example 2 were each formed as a film on a 1.1 mm thick quartz substrate by spin coating and baked at 200° C. for 60 minutes. The film thickness was set at 30 nm. The UV-VIS spectra of the thin film on the quartz substrate were measured. The spectra were measured by scanning over 40 to 800 nm in the visible region. The results are shown in FIG. 1.

As shown in FIG. 1, the UV-VIS spectra were measured in the form of a charge-transporting thin film actually used in an organic EL device, with the result that it was found that the transmittances in the visible region (400 to 800 nm) of the charge-transporting thin film formed of the aniline compounds of the type wherein a different structure was introduced into the repeating units were higher than that of PTA.

More particularly, when comparison is made at 800 nm, Example 7 is improved in transmittance by 8.59% over Comparative Example 2 and Example 8 is improved by 13.48% over Comparative Example 2. When comparison is made at 600 nm, Example 7 is improved in transmittance by 9.14% over Comparative Example 2 and Example 8 is improved by 7.30% over Comparative Example 2. Moreover, when comparison is made at 400 nm, Example 7 is improved in transmittance by 3.26% over Comparative Example 2 and Example 8 is improved by 9.88% over Comparative Example 2.

From the results of Tables 3 to 5 and FIG. 1, it has been found that if the oligoaniline compounds of the invention wherein a structure different from aniline units is introduced into the aniline units serving as repeating units have a conjugated system partially cut off in the molecule, or have a conjugated system constituted of a different repeating unit structure, electric conductivity does not lower when formed as a charge-transporting thin film. In addition, the compounds in a solid state or in a charge-transporting vanish wherein an acceptor is doped, exhibit high L* and an improved transmittance in the visible region in a state of a thin film used as a charge-transporting thin film.

Accordingly, it has been expected that the charge-transporting thin film, which is formed by use of a charge-transporting vanish containing an oligoaniline compound of the invention and is suppressed from coloration, functions as an excellent charge-transporting material for organic EL devices.

The invention claimed is:

1. An oligoaniline compound, characterized by being represented by the formula (1)

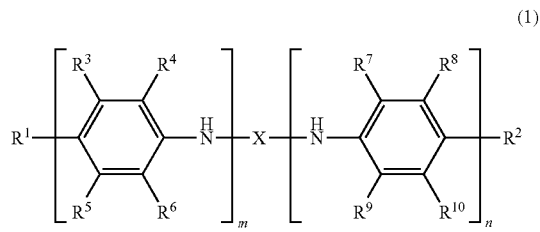

wherein $R^1$ to $R^{10}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, m and n are independently an integer of 1 or over provided that $4 \leq m+n \leq 20$ is satisfied, and X represents any of groups represented by the following formulas (5) to (14), (14-1), (14-2), and (15) to (21)

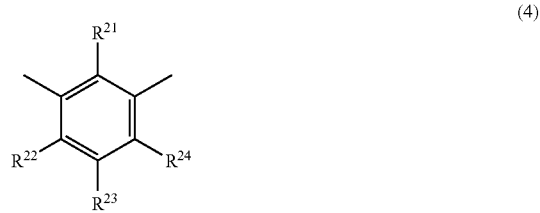

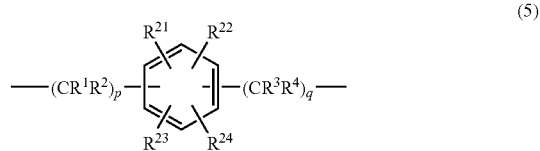

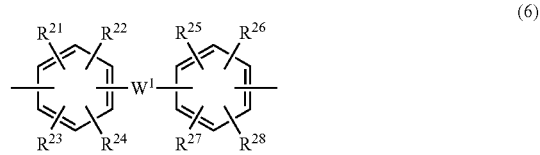

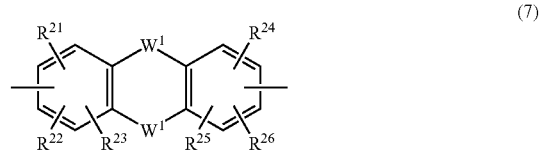

-continued

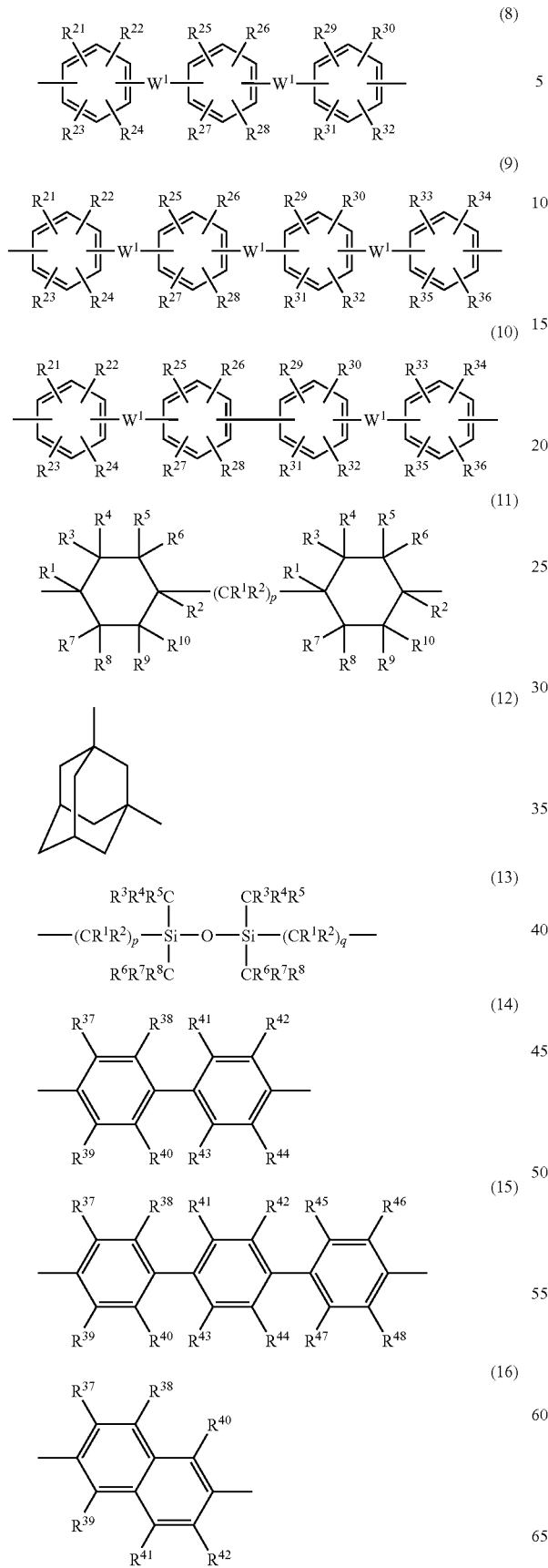

wherein $R^1$ to $R^{10}$, respectively, have the same meanings as defined above, $R^{21}$ to $R^{52}$ independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, p and q are independently an integer of 1 or over provided that $p \leq 20$ and $q \leq 20$ are satisfied, $W^1$'s independently represent —$(CR^1R^2)_p$—, —O—, —S—, —S—S—, —S(O)$_2$—, —C(O)—, —C(O)O—, —OC(O)—, —C(S)O—, —OC(S)—, —C(O)NR$^1$—, —NR$^1$C(O)—, —O—$(CR^1R^2)_p$—O—, —C(O)O—$(CR^1R^2)_p$—OC(O)—, —O—Si$(CR^1R^2)_2$—O—, wherein $R^1$, $R^2$ and p, respectively, have the same meanings as defined above, a group represented by the following formula (22), or a group represented by the following formula (23)

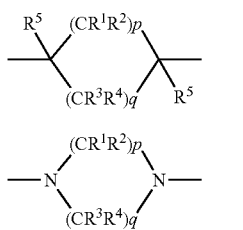

(22)

(23)

wherein $R^1$ to $R^5$, p and q, respectively, have the same meanings as defined above.

2. An oligoaniline compound, characterized by being represented by the formula (2)

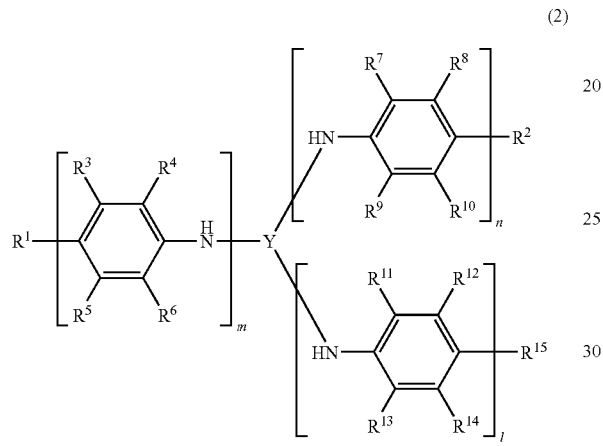

(2)

wherein $R^1$ to $R^{15}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, m, n and l are independently an integer of 1 or over provided that $m+n+l \leq 20$ is satisfied, and Y represents a group represented by the following formula (24) or (25)

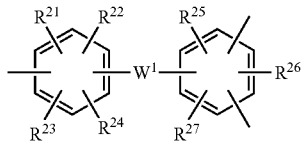

(24)

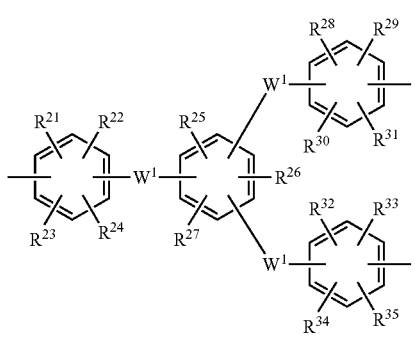

(25)

wherein $R^{21}$ to $R^{35}$ independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, and $W^1$s independently represent $-(CR^1R^2)_p-$, $-O-$, $-S-$, $-S-S-$, $-S(O)_2-$, $-NR^1-$, $-C(O)-$, $-C(O)O-$, $-OC(O)-$, $-C(S)O-$, $-OC(S)-$, $-C(O)NR^1-$, $-NR^1C(O)-$, $-O-(CR^1R^2)_p-O-$, $-C(O)O-(CR^1R^2)_p-OC(O)-$, $-O-Si(CR^1R^2)_2-O-$, wherein $R^1$, $R^2$ and p, respectively, have the same meanings as defined above, a group represented by the following formula (22), or a group represented by the following formula (23)

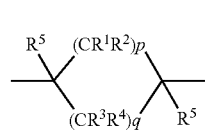

(22)

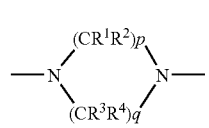

(23)

wherein $R^1$ to $R^5$, respectively, have the same meanings as defined above, and p and q are, respectively, an integer of 1 or over provided that $p \leq 20$ and $q \leq 20$ are satisfied.

3. An oligoaniline compound, characterized by being represented by the formula (3)

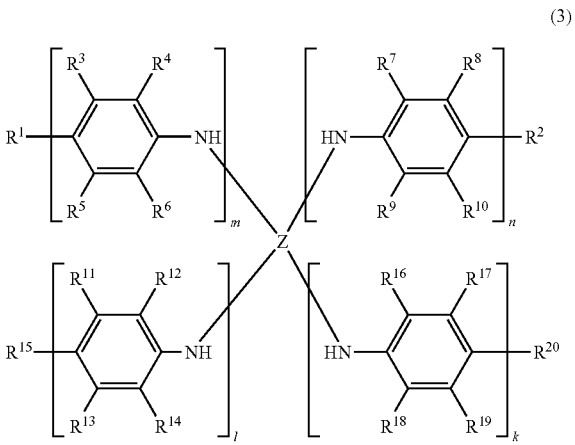

(3)

wherein $R^1$ to $R^{20}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, m, n, l and k are independently an integer of 1 or over provided that $m+n+l+k \leq 20$ is satisfied, and Z represents a group represented by the following formula (26) or (27)

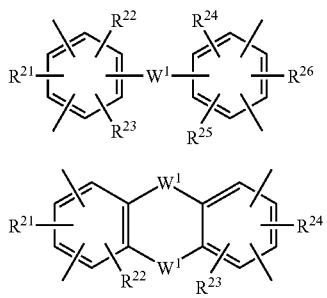

(26)

(27)

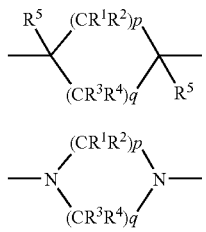

(22)

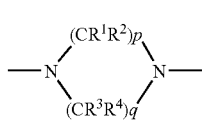

(23)

wherein $R^{21}$ to $R^{26}$ independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, and $W^1$s independently represent —$(CR^1R^2)_p$—, —O—, —S—, —S—S—, —S(O)$_2$—, —NR$^1$—, —C(O)—, —C(O)O—, —OC(O)—, —C(S)O—, —OC(S)—, —C(O)NR$^1$—, —NR$^1$C(O)—, —O—$(CR^1R^2)_p$—O—, —C(O)O—$(CR^1R^2)_p$—OC(O)—, —O—Si(CR$^1$R$^2$)$_2$—O—, wherein $R^1$, $R^2$ and p, respectively, have the same meanings as defined above, a group represented by the following formula (22), or a group represented by the following formula (23)

wherein $R^1$ to $R^5$, respectively, have the same meanings as defined above, and p and q are, respectively, an integer of 1 or over provided that p≤20 and q≤20 are satisfied.

4. The charge transport material made of the oligoaniline compound defined in any one of claims 1 to 3.

5. The charge-transporting varnish comprising the oligoaniline compound defined in any one of claims 1 to 3.

6. The charge-transporting thin film formed from the charge-transporting varnish of claim 5.

7. The charge-transporting thin film comprising the oligoaniline compound defined in any one of claims 1 to 3.

8. The organic electronic device comprising at least one layer of the charge-transporting thin film defined in claim 6.

9. The organic electroluminescent device comprising at least one layer of the charge-transporting thin film defined in claim 6.

10. The organic electroluminescent device defined in claim 9, wherein said charge-transporting thin film serves as a hole injection layer or a hole transport layer.

* * * * *